US00PP14537P39

(12) United States Plant Patent
Elsley

(10) Patent No.: US PP14,537 P3
(45) Date of Patent: Feb. 17, 2004

(54) **CHINESE *ANGUSTATA* DOGWOOD NAMED 'ELSBRY'**

(50) Latin Name: *Cornus angustata*
Varietal Denomination: Elsbry

(76) Inventor: John E. Elsley, 520 Bryte St., Greenwood, SC (US) 29649

( * ) Notice: Subject to any disclaimer, the term of this patent is extended or adjusted under 35 U.S.C. 154(b) by 0 days.

(21) Appl. No.: 10/103,003

(22) Filed: Mar. 21, 2002

(65) Prior Publication Data

US 2003/0182698 P1 Sep. 25, 2003

(51) Int. Cl.[7] ..... A01H 5/00
(52) U.S. Cl. ..... Plt./220
(58) Field of Search ..... Plt./220

(56) References Cited

U.S. PATENT DOCUMENTS

| | | | | |
|---|---|---|---|---|
| PP4,242 | P | 4/1978 | Blow et al. | Plt./220 |
| PP4,444 | P | 7/1979 | Handy | Plt./220 |
| PP4,869 | P | 7/1982 | Boyd | Plt./220 |
| PP6,305 | P | 9/1988 | Nicholson | Plt./220 |
| PP6,320 | P | 10/1988 | Nicholson | Plt./220 |
| PP7,204 | P | 3/1990 | Orton, Jr. | Plt./220 |
| PP7,205 | P | 3/1990 | Orton, Jr. | Plt./220 |
| PP7,206 | P | 3/1990 | Orton, Jr. | Plt./220 |
| PP7,210 | P | 4/1990 | Orton, Jr. | Plt./220 |
| PP7,732 | P | 12/1991 | Orton, Jr. | Plt./220 |
| PP7,766 | P | 1/1992 | Rawdon | Plt./220 |
| PP8,213 | P | 4/1993 | Orton, Jr. et al. | Plt./220 |
| PP8,214 | P | 4/1993 | Orton, Jr. et al. | Plt./220 |
| PP8,500 | P | 12/1993 | Smith | Plt./220 |
| PP8,675 | P | 4/1994 | Yamashita et al. | Plt./220 |
| PP8,703 | P | 4/1994 | Devine | Plt./220 |
| PP9,283 | P | 9/1995 | Schmidt | Plt./220 |
| PP10,166 | P | 12/1997 | Nicholson | Plt./220 |
| PP10,423 | P | 6/1998 | Stanley | Plt./220 |
| PP11,287 | P | 3/2000 | Stackman | Plt./220 |
| PP11,654 | P | 11/2000 | Asako | Plt./220 |

*Primary Examiner*—Kent Bell
(74) *Attorney, Agent, or Firm*—McNair Law Firm, P.A.

(57) ABSTRACT

A new and distinct cultivar of evergreen Dogwood tree named 'Elsbry' that is particularly characterized by the unique combination of its vigorous growth rate, flowering at a young age, prolific flower production on an annual basis, blooms 2–3 weeks later and over a longer period than other Dogwood selections, fruits extend ornamental interest into the early fall season, increased disease resistance, and good cold hardiness.

4 Drawing Sheets

Variety denomination: *Cornus angustata* 'Elsbry'.

BACKGROUND OF THE INVENTION

The present invention relates to a new and distinct cultivar of Chinese evergreen dogwood *Cornus angustata*, hereinafter referred to by the cultivar name 'Elsbry'. Prior to the designation of *Cornus angustata* as a distinct species in 1994, by Dr. T. R. Dudley of the United States National Arboretum, Washington, D.C. (see Phytologia. Vol. 76, pg. 428, 1994), *Cornus angustata* was classified as a variety of the Chinese kousa Dogwood, *Cornus kousa*, variety *angustata* Chun 1934.

The new 'Elsbry' variety of Dogwood was obtained by the Inventor in 1993 as a two to three year old seedling from a cultivated area in a Greenwood, S.C. nursery. It is believed that the seedling originated from seed collected in China. The plant has been cultivated in the Greenwood, S.C. garden of the Inventor where it was recognized to be a new and distinct cultivar of *Cornus angustata* having the unique characteristics described herein below.

Asexual reproduction of the new Dogwood by grafting and budding on seedling *Cornus kousa* and *Cornus florida* understocks has been undertaken at locations in Winchester and Belvidere, Tenn., and by softwood cutting in Hodges, S.C., which has shown in all instances that the unique features of the new 'Elsbry' Dogwood are stable and reproduced true to type in successive generations.

SUMMARY OF THE INVENTION

Plants of the new 'Elsbry' Dogwood have not been observed under all possible environmental conditions. Accordingly, the phenotype may vary somewhat depending on changes in environmental conditions such as temperature, daylight, light intensity, nutrition and water status, without however, any variance in genotype. The following traits have been repeatedly observed and are determined to be the unique characteristics of 'Elsbry'. The following characteristics in combination distinguish 'Elsbry' as a new and distinct cultivar of *Cornus angustata:*

1. Vigorous growth rate.
2. Flowers produced at a young age, specifically, on 2 year old grafted plants.
3. Prolific flowering on an annual basis, specifically, heavier than other selections of *Cornus angustata* known to the Inventor.
4. Blooms 2 to 3 weeks later and over a larger period than other *Cornus angustata* and *Cornus kousa* Dogwood selections known to the inventor. In Greenwood, S.C. flowering commences in early May lasting through mid to late June.
5. Fruits form in early to mid September, extending ornamental interest into the fall season.
6. The evergreen foliage displays resistance to powdery mildew, as well as leaf and stem anthracnose, two major disease problems affecting many Dogwoods.

7. Foliage retention and deep green foliage coloration are maintained during the fall and winter months better than other selections of *Cornus angustata* known and observed by the Inventor.
8. Exhibits good cold hardiness, having withstood temperatures as low as 0° F. in Winchester, Tenn. The typical and observed hardiness zone ranges from between 6b to 9 on the U.S. Department of Agriculture Plant Hardiness Zone Map (1990).

BRIEF DESCRIPTION OF THE PHOTOGRAPHS

The accompanying colored photographs illustrate the overall appearance of the new 'Elsbry' Dogwood showing the colors as true as it is reasonably possible to obtain in colored reproductions of this type. All photographs depicting the new 'Elsbry' were taken of the plant growing in a cultivated area of Greenwood, S.C.

DETAILED BOTANICAL DESCRIPTION

Figure 1:
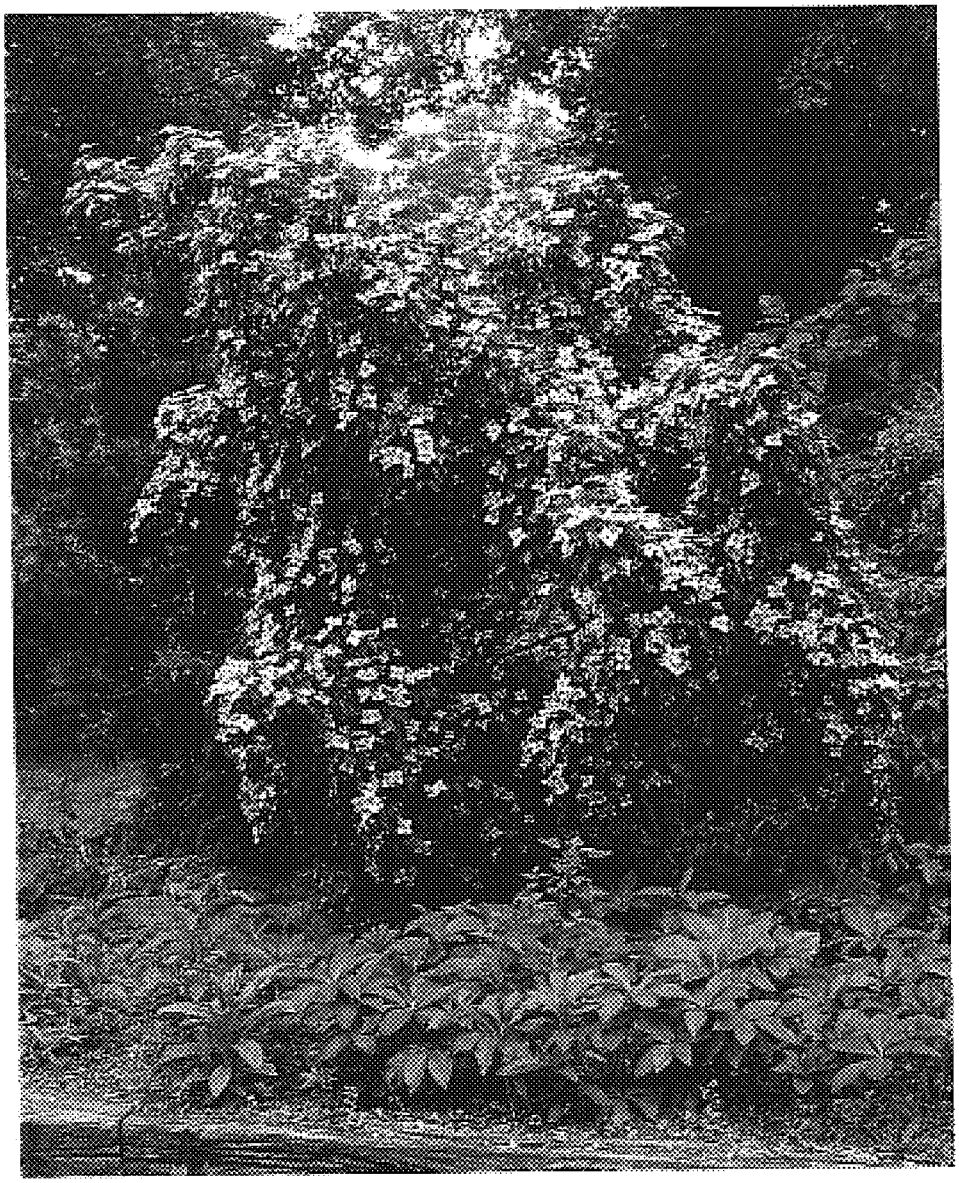
FIG. 1, shows the entire plant in full bloom.
Figure 2:
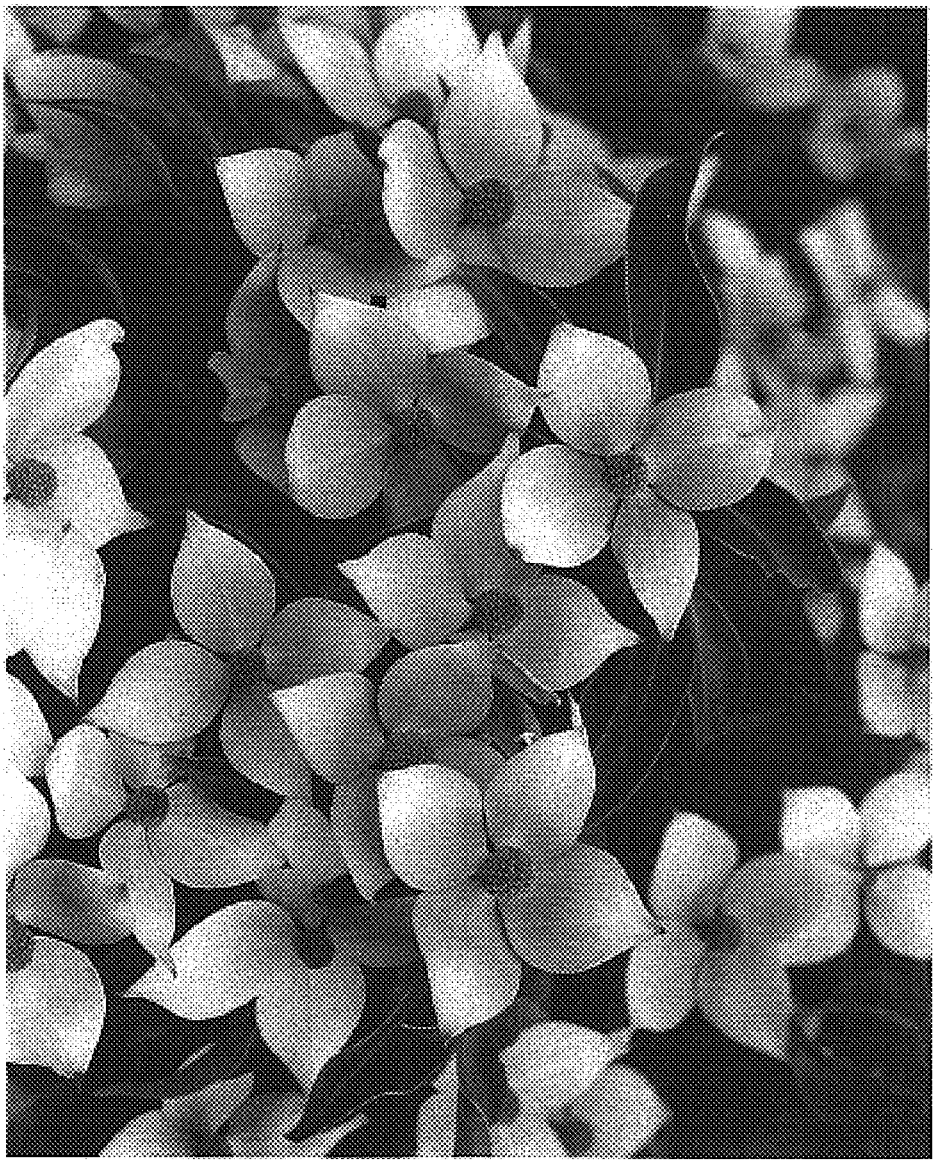
FIG. 2, shows a detailed close up of the flowers and foliage.
Figure 3:
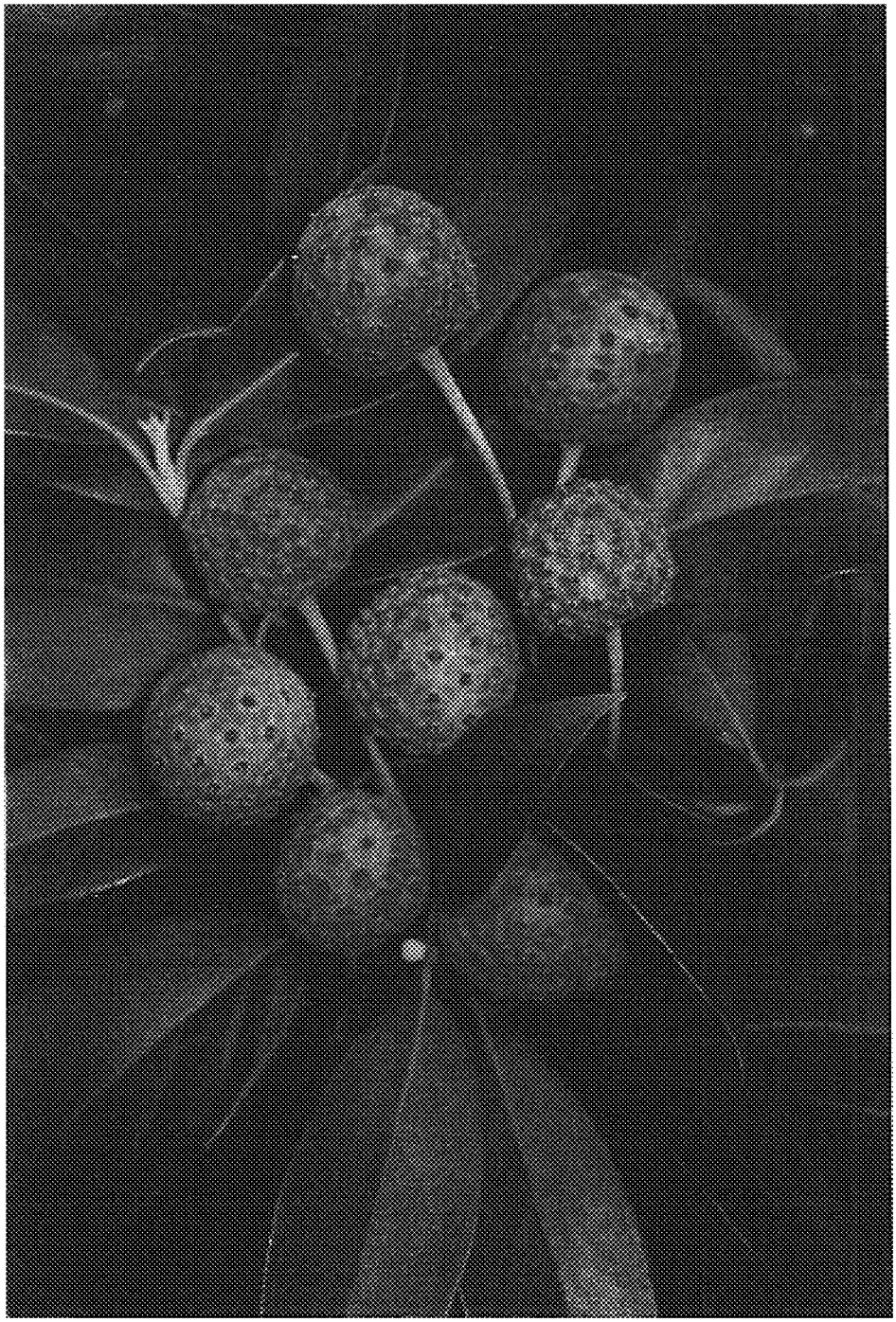
FIG. 3, shows the fruits typically produced in the month of September.
Figure 4:
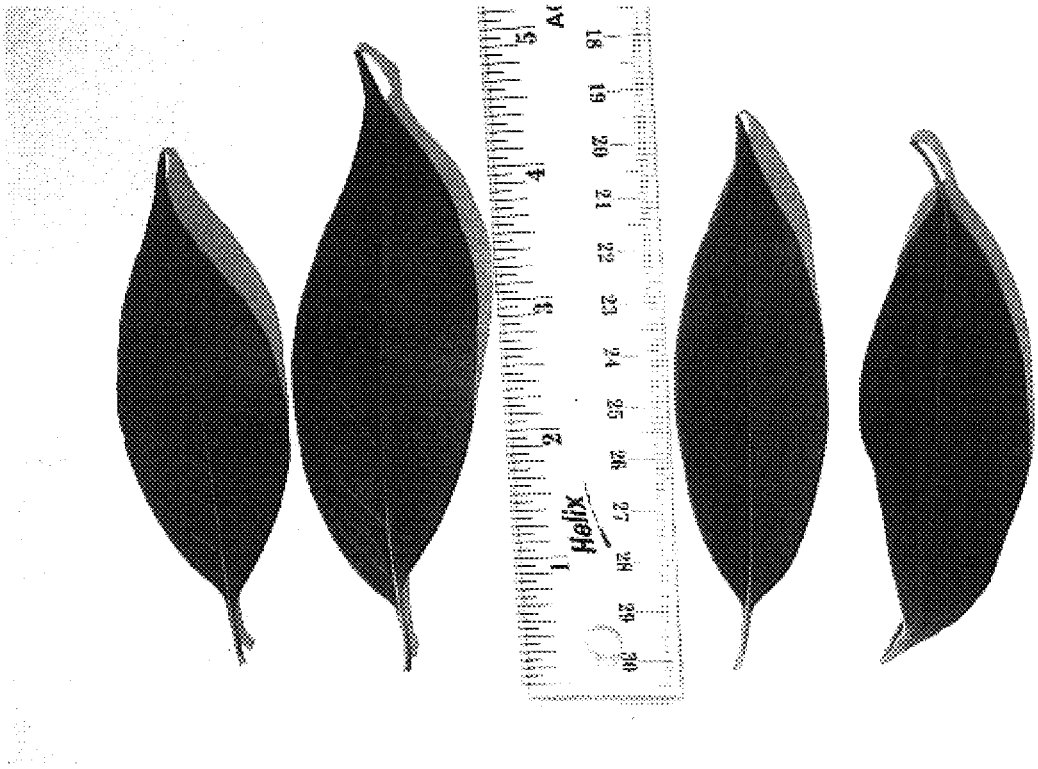
FIG. 4, shows several mature leaves against a ruler to provide a reference for illustrating foliage characteristics and dimensions.

The following observations, measurements and values were obtained from the original ten to twelve year old plant obtained in 1993 growing in a cultivated area on the property of the Inventor in Greenwood, S.C. The characteristics described herein are known to apply to other plants of the 'Elsbry' variety grown under similar soil and climate conditions. In the following description, color references are made to The Royal Horticultural Society Colour Chart (London, 1966), except where general terms of ordinary dictionary significance are used.

Botanical classification: *Cornus angustata* cultivar 'Elsbry'.

Propagation: (1) Chip or T budding during August and September on seedling, *Cornus florida* or *Cornus kousa* understocks. (2) Terminal softwood cuttings from April through December. (3) Rooting occurs from six to eight weeks in a controlled, enclosed environment within 80% to 90% relative humidity and 80° F. to 82° F. Cuttings are pretreated with a basil application of a 0.5% I.B.A. (Indole 3 butyric acid).

Plant description:

*Plant form and growth habit.*—Perennial evergreen, multi-stemmed tree, vase shaped when young, becoming more rounded and spreading with age.

*Vigor.*—Slow to medium in early years with 10 to 15 cm of new growth per year, becoming more vigorous with age, leading to 25 to 35 cm of new growth per year after the first 10 to 12 years.

*Plant size.*—10 to 12 year old plants have a height of approximately 4 meters and a width of approximately 4 meters under outdoor conditions in Greenwood, S.C.

*Branching habit.*—Moderate, branch crotch angles of between 45° to 60° to main trunk.

*Trunk description.*—Diameter is approximately 15 cm at soil level, reducing to approximately 7 cm at 30 cm above soil level. Bark texture is rough. Bark color being grayed-green closest to color 195B, with prominent gray-brown closest to color 199D lenticels.

*Lateral branch description.*—Diameter approximately 3 cm at 1 meter above the soil level. Bark texture being rough. Bark color closest to gray-brown 199D with prominent gray-green closest to 198D lenticels.

Foliage description:

*Arrangement.*—Simple, opposite, mainly crowded towards branch apices.

*Length.*—Approximately 12 cm.

*Width.*—Approximately 3 to 4 cm.

*Petiole length.*—Approximately 1.5 cm.

*Petiole diameter.*—Approximately 1.5 mm.

*Petiole color.*—Yellow-green closest to 145B.

*Shape.*—Elliptical to oval.

*Apex.*—Acuminate.

*Base.*—Cuneate.

*Margin.*—Entire, slightly undulating towards apex.

*Texture.*—Upper surface being glossy and lustrous, ciliated with numerous minute white hairs pressed against surface. Lower surface being dulled, non-lustrous and also ciliated with numerous minute white hairs pressed against surface and along the prominent raised veins.

*Color.*—Young leaves having an upper surface uniform green closest to 143C. The lower surface being uniform yellow-green closest to 148D. Mature leaves having an upper surface uniform dark green closest to 139A with a paler distinct yellow-green prominent mid-rib closest to 145A. The lower surface being uniform gray-green closest to 191B with a paler prominent raised yellow-green mid-rib closest to 145D.

Flower description:

*Natural flowering season.*—Late spring into early summer, particularly the months of May through June as observed in from the plant in Greenwood, S.C. Young flowers bud 5 mm linear bracts 1 cm long, closest to color green 131B on erect 7 mm peduncles visible in mid October.

*Inflorescence arrangement.*—60 to 80 flowers arranged in dense, globose terminal cymes, 1 cm in diameter being yellow-green closest to color 148C. Flowers subtended by a corolla-like involucre of four showy bracts. Single non-fragrant inflorescences are densely massed on the terminal sections of branches.

*Inflorescence diameter.*—Approximately 6 to 7 cm.

*Inflorescence depth.*—About 5 to 6 mm.

*Peduncle.*—Erect about 7 cm long and 2 mm in diameter, yellow-green in color closest to 145B.

*Involucral bracts.*—Four oval to obovate acuminate apex being purple-violet closest to color 82B, and between 4 to 5 cm long, 3 to 3.5 cm wide. Young bracts being bi-colored with an upper surface having a lower half yellow-green color closest to 145B, shifting to yellow-green color closest to 150D towards apex. At maturity, the upper surface being uniformly yellow-green color close to 150D. The lower surface of young bracts being uniformly yellow-green closest to 150D, and at maturity being uniformly yellow-white closest to color 158D.

*Sepals.*—Typically 4, minute, approximately 1 mm wide and approximately 1.5 mm long, yellow-green closest to 148C.

*Petals.*—Typically 4, ovate, spreading, upper surface concave toward apex, approximately 2.5 mm long and 1.0 mm wide, having similar color on upper and lower surfaces with the basal half being yellow-green closest to 150C, and the terminal half being yellow-green closest to 145B.

*Stamens.*—Typically 4, protruding, approximately 2 mm long with a generally pale whitish color.

*Pollen.*—Generally yellow-brown.

*Pistil.*—Typically 1, style being columnar, simple, stigma, capitate, approximately 1.5 mm to 2 mm with a generally greenish-white color.

*Ovary.*—Inferior, 2-locular, 1 seed per locule, approximately 1 mm to 1.5 mm, being pale white.

Fruit description:

*Type.*—Fruits are 2-celled, one seeded, fleshy, drupes, forming a raspberry syncarp, and maturing in early fall, approximately mid September as observed in Greenwood, S.C.

*Shape.*—Syncarp globose, terminally positioned on an approximately 6 cm long pendulous peduncle.

*Diameter.*—Approximately 2 cm for syncarp.

*Length.*—Approximately 2 cm for globose.

*Color.*—Orange-red closest to 33A.

*Seed.*—Ellipsoidal, smooth.

Disease resistance: Resistance to powdery mildew and leaf and stem anthracnose diseases which commonly affect related Dogwoods.

What is claimed is:

1. A new and distinct variety of Dogwood tree named 'Elsbry', as illustrated and described.

* * * * *